(12) United States Patent
Liu et al.

(10) Patent No.: US 10,806,364 B2
(45) Date of Patent: Oct. 20, 2020

(54) METHODS AND APPARATUSES FOR ELECTROOCULOGRAM DETECTION, AND CORRESPONDING PORTABLE DEVICES

(71) Applicant: Beijing Zhigu Rui Tuo Tech Co., Ltd, Beijing (CN)

(72) Inventors: Hao Liu, Beijing (CN); Wei Shi, Beijing (CN)

(73) Assignee: Beijing Zhigu Rui Tuo Tech Co., Ltd, Beijing (CN)

( * ) Notice: Subject to any disclaimer, the term of this patent is extended or adjusted under 35 U.S.C. 154(b) by 681 days.

(21) Appl. No.: 15/321,692

(22) PCT Filed: Jun. 5, 2015

(86) PCT No.: PCT/CN2015/080843
§ 371 (c)(1),
(2) Date: Dec. 22, 2016

(87) PCT Pub. No.: WO2015/196918
PCT Pub. Date: Dec. 30, 2015

(65) Prior Publication Data
US 2017/0150898 A1    Jun. 1, 2017

(30) Foreign Application Priority Data
Jun. 27, 2014 (CN) .......................... 2014 1 03017837

(51) Int. Cl.
*A61B 5/0496* (2006.01)
*A61B 5/00* (2006.01)

(52) U.S. Cl.
CPC .......... *A61B 5/0496* (2013.01); *A61B 5/6803* (2013.01)

(58) Field of Classification Search
CPC ... A61B 5/0496; A61B 5/6803; A61B 5/1103; A61B 5/163; A61B 3/10; A61B 3/113;
(Continued)

(56) References Cited

U.S. PATENT DOCUMENTS 5,517,021 A  *  5/1996  Kaufman .............. A61B 3/113
                                                          250/221
8,405,610 B1     3/2013  Cole
(Continued)

FOREIGN PATENT DOCUMENTS

CN        101599127 A       12/2009
CN        101995944 A        3/2011
(Continued)

OTHER PUBLICATIONS

Kaneko, Kenichi et al. "Evaluation of Three Types of Blinks with the Use of Electro-Oculogram and Electromyogram", Perceptual and Motor Skills, 1999, 88, 1037-1052 (Year: 1999).*
(Continued)

*Primary Examiner* — Matthew Kremer
*Assistant Examiner* — Avery M Foley
(74) *Attorney, Agent, or Firm* — Amin, Turocy & Watson, LLP

(57) ABSTRACT

Electrooculogram (EOG) detection methods and EOG detection apparatuses are described. The EOG detection method can comprise: acquiring at least one EOG signal of a blink of at least one eye of a user; and analyzing the at least one EOG signal to determine whether the blink is a protective blink. A basis is thus provided for further applications of an eye movement detection technology by determining, according to an EOG signal of a user, whether a blink of the user is a protective blink.

20 Claims, 6 Drawing Sheets

(58) Field of Classification Search
CPC ........... A61B 2017/00216; G06F 3/013; G06F 3/015; G06F 3/011; G06F 3/01; G06F 1/163; G06F 2203/04801; G06N 20/00; G06N 20/10
See application file for complete search history.

(56) References Cited

U.S. PATENT DOCUMENTS

| | | | |
|---|---|---|---|
| 9,274,599 B1* | 3/2016 | D'Amico | G06F 3/013 |
| 2013/0329183 A1* | 12/2013 | Blum | G02C 11/10 |
| | | | 351/158 |
| 2014/0243971 A1* | 8/2014 | Pugh | G02C 7/04 |
| | | | 623/6.22 |

FOREIGN PATENT DOCUMENTS

| | | |
|---|---|---|
| CN | 102125429 A | 7/2011 |
| CN | 101599127 B | 9/2011 |
| CN | 103054549 A | 4/2013 |
| CN | 203379122 U | 1/2014 |
| CN | 104049761 A | 9/2014 |

OTHER PUBLICATIONS

International Search Report for PCT Application No. PCT/CN2015/080843, dated Sep. 11, 2015, 3 pages.

Yue, Chongshi. "EOG Signals in Drowsiness Research" http://www.diva-portal.org/smash/get/diva2:555912/FULLTEXT01.pdf, Dec. 10, 2012 (Dec. 10, 2012), 59 pages.

\* cited by examiner

METHODS AND APPARATUSES FOR ELECTROOCULOGRAM DETECTION, AND CORRESPONDING PORTABLE DEVICES

RELATED APPLICATION

The present application is a U.S. National Stage filing under 35 U.S.C. § 371 of international patent cooperation treaty (PCT) application No. PCT/CN2015/080843, filed Jun. 5, 2015, entitled "METHODS AND APPARATUSES FOR ELECTROOCULOGRAM DETECTION, AND CORRESPONDING PORTABLE DEVICES", which claims the benefit of priority to Chinese Patent Applications No. 201410301783.7, filed on Jun. 27, 2014, which applications are hereby incorporated into the present application by reference herein in their respective entireties.

TECHNICAL FIELD

The present application relates to an eye movement detection technology, and in particular, to electrooculogram (EOG) detection methods and EOG detection apparatuses.

BACKGROUND

With a higher requirement of users on portability, many personal electronic devices become smaller and smaller, and interaction with users cannot be implemented conveniently and naturally by using a mouse, a key, or a touch panel only. Therefore, function modules such as virtual projection interaction, voice interaction, and eye-control interaction are used in more and more electronic devices. As one of the eye-control interaction technologies, the EOG detection interaction technology is also used to generate corresponding control instructions. For example, an electronic device such as smart glasses uses a blink of a user as a control input, to avoid a complex process of using a camera button or a voice command, making it more convenient for users to use the electronic device.

SUMMARY

An example, non-limiting objective of the present application is to provide an EOG detection solution.

According to a first aspect, an example embodiment of the present application provides an EOG detection method, comprising:
   acquiring at least one EOG signal of a blink of at least one eye of a user; and
   analyzing the at least one EOG signal to determine whether the blink is a protective blink.

According to a second aspect, an example embodiment of the present application provides an EOG detection apparatus, comprising:
   an EOG signal acquiring module, configured to acquire at least one EOG signal of a blink of at least one eye of a user; and
   a blink determining module, configured to analyze the at least one EOG signal to determine whether the blink is a protective blink.

At least one of the example embodiments of the present application provides a basis for further applications of an eye movement detection technology by determining, according to an EOG signal of a user, whether a blink of the user is a protective blink. For example, in an example embodiment, when a device control command can be generated by detecting blink actions of a user, the protective blink is excluded from valid control commands, so that an EOG command can be recognized more accurately.

DETAILED DESCRIPTION

Figure 1:
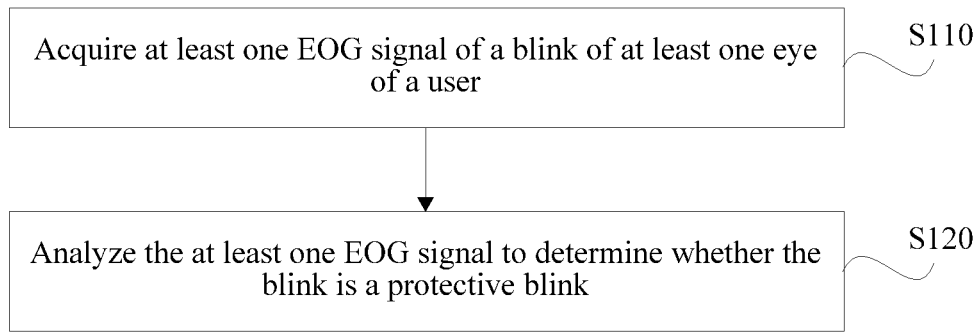
FIG. 1 is a flowchart of steps of an EOG detection method according to an example embodiment of the present application.

Example embodiments of the present application are described in further detail below with reference to the accompanying drawings (where identical reference numerals in several accompanying drawings represent identical elements). The following embodiments are used for describing the present application, but are not intended to limit the scope of the present application.

A person skilled in the art can understand that terms such as "first" and "second" in the present application are merely used for distinguishing different steps, devices, or modules, but neither represent any specific technical content nor represent any necessary logic sequence between steps, devices, or modules.

In the following description of the embodiments of the present application, the "protective blink" is a stress protective blink performed by a user against a sudden external stimulus, for example, the entering of a small foreign matter, the exposure to strong light, and the threat of an object coming to the eye will cause the protective blink; the "directive blink" is a conscious blink performed by a user to send a control signal to a device, for example, a user sends a predetermined control signal by blinking the right eye, so that a device such as smart glasses generates a corresponding control instruction, for example, taking a photo; the "unconscious blink" is a regular blink that a user performs to moisturize eyeballs out of a physiological directive, where the user generally have 10 to 20 such blinks per minute unconsciously.

In general EOG control applications, when an EOG detection technology is used to classify blinks of a user, the protective blink is not distinguished, for example, in some example embodiments, the protective blink is classified as the directive blink. Therefore, as shown in FIG. 1, an example embodiment of the present application provides an EOG detection method, which comprises the following steps:

S110: Acquire at least one EOG signal of a blink of at least one eye of a user.

S120: Analyze the at least one EOG signal to determine whether the blink is a protective blink.

For example, an EOG detection apparatus provided by the present application is used as an entity for executing this embodiment, to execute steps S110 to S120. Specifically, the EOG detection apparatus may be set in a user equipment in a form of software, hardware, or a combination of hardware and software, or the EOG detection apparatus is the user equipment; the user equipment comprises, but is not limited to: a smart phone, smart glasses, an smart helmet, and the like.

In one or more embodiments of the present application, the EOG signal corresponding to the protective blink has some characteristics, for example, the blink is highly intense, and the eye is closed quickly and opened slowly; therefore, by analyzing the at least one EOG signal, it can be determined whether the blink is a protective blink, thereby distinguishing the protective blink from multiple types of blinks of the user, to provide a basis for further applications related to the protective blink.

The steps of the method in this embodiment of the present application are further described by using the following example embodiments.

S110: Acquire at least one EOG signal of a blink of at least one eye of a user.

In this embodiment of the present application, multiple methods may be used in step S110 to acquire the at least one EOG signal, for example, the method is one of the following:

1) Collect the at Least One EOG Signal.

In this example embodiment, for example, an EOG sensing device of the EOG detection apparatus may be used to collect the at least one EOG signal.

When a blink of only one eye of the user can be detected, an EOG signal of the blink of one eye (left eye or right eye) of the user is acquired in step S110, where the EOG sensing device may be a monocular EOG sensing device, such as a left-eye EOG sensing device; when blinks of both eyes of the user are to be detected, two EOG signals of the blinks of two eyes of the user are acquired in step S110, where the EOG sensing device is a binocular EOG sensing device.

2) Receive the at Least One EOG Signal from an External Device.

In this example embodiment, for example, a communication module of the EOG detection apparatus may be used to receive the at least one EOG signal from at least one external device. For example, the EOG detection apparatus may be set in a user equipment such as a mobile phone or a smart watch, and the user further wears an EOG collecting apparatus, where the EOG detection apparatus may obtain the EOG signal from the EOG collecting apparatus.

S120: Analyze the at least one EOG signal to determine whether the blink is a protective blink.

Figure 2:
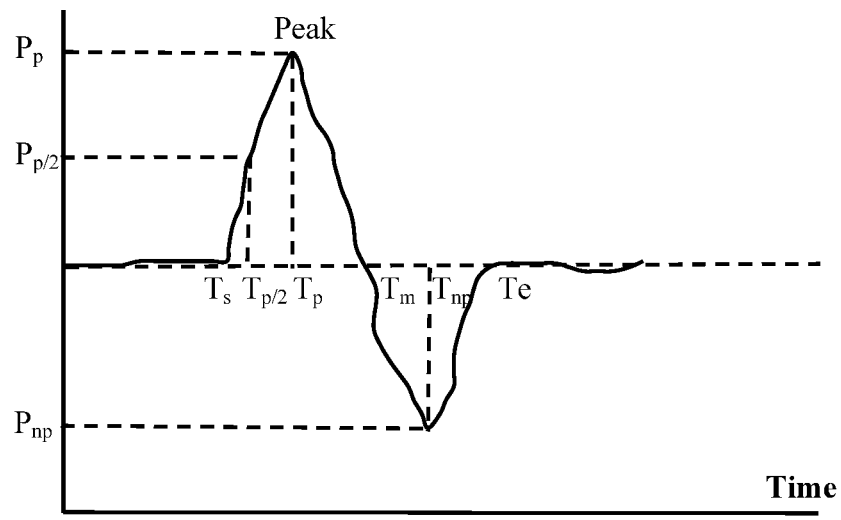
FIG. 2 is a schematic diagram of a waveform and a characteristic point of an example EOG signal.

As shown in FIG. 2, the EOG signal of one blink generally may have the waveform shown in FIG. 2, where the waveform is a curve showing an amplitude of EOG signal changing with time. As mentioned above, the protective blink has its own characteristics, and the EOG signal corresponding to the protective blink also has its own characteristics; therefore, in this embodiment of the present application, step S120 may further comprise:

obtaining at least one eigenvalue according to the at least one EOG signal; and performing matching on the at least one eigenvalue according to at least one reference eigenvalue, to determine whether the blink is the protective blink.

In this embodiment of the present application, the at least one eigenvalue comprises at least one of the following:

at least one amplitude characteristic of at least one characteristic point of the at least one EOG signal, and at least one time characteristic of at least one characteristic point of the at least one EOG signal.

The at least one eigenvalue may comprise only one eigenvalue, or comprise multiple eigenvalues. When the at least one eigenvalue comprises multiple eigenvalues, the multiple eigenvalues may be multiple amplitude characteristics separately corresponding to multiple characteristic points; or, the multiple eigenvalues may be multiple time characteristics separately corresponding to multiple characteristic points; or at least one eigenvalue of the multiple eigenvalues is at least one amplitude characteristic of at least one characteristic point, and other eigenvalue(s) is(are) time characteristic(s) of at least one characteristic point. Herein, the at least one characteristic point corresponding to the amplitude characteristic may be the same as or different from the at least one characteristic point corresponding to the time characteristic.

For example, in an example embodiment, the characteristic point may be a wave crest of the EOG signal, and the at least one eigenvalue may be an amplitude characteristic corresponding to the wave crest.

For another example, in another example embodiment, the at least one eigenvalue comprises: a time characteristic corresponding to a characteristic point at the beginning of a blink, an amplitude characteristic and a time characteristic of a characteristic point where an amplitude value reaches ½ of a peak value, an amplitude characteristic and a time characteristic corresponding to a wave crest, and the like.

The embodiment shown in FIG. 2 provides characteristic points that may be used in the EOG signal and eigenvalues of the characteristic points, comprising:

time $T_s$ corresponding to a waveform starting point of a blink, amplitude $P_{p/2}$ and time $T_{p/2}$ corresponding to a point where an amplitude value reaches ½ of the peak value, amplitude value $P_p$ and time $T_p$ corresponding to the wave crest (Peak), time $T_m$ corresponding to a point where an amplitude value declines to 0, amplitude value $P_{np}$ and time $T_{np}$ corresponding to the trough, and time $T_e$ corresponding to a waveform end point of the blink. Certainly, a person skilled in the art may know that, a user may also use other eigenvalues corresponding to other possible characteristic points as required, for example, an amplitude value and time corresponding to a point where the amplitude value reaches ¼ of the peak value, or a slope of a given characteristic point.

In this embodiment of the present application, the at least one reference eigenvalue may be a preset value acquired from a storage module of the EOG detection apparatus, or may be obtained by means of learning training (refer to the corresponding description in the following embodiment). The at least one reference eigenvalue may be a value corresponding to the at least one eigenvalue. For example, when the eigenvalue is the amplitude value of the peak, the at least one reference eigenvalue may be one or more reference amplitude values, and during the matching, the amplitude value of the peak may be compared with the one or more reference amplitude values.

Certainly, in other example embodiments, the at least one reference eigenvalue may also be a parameter of a classification model for distinguishing different types of blinks comprising the protective blink; the matching may be performed by inputting the at least one eigenvalue to the classification model to obtain a result indicating whether the blink is the protective blink.

In this embodiment of the present application, the at least one reference eigenvalue is generally multiple reference eigenvalues, for example, multiple reference eigenvalues corresponding to the multiple eigenvalues shown in FIG. 2, and matching is performed on each eigenvalue to determine whether the blink is the protective blink.

As described above, the at least one reference eigenvalue may be obtained by means of learning training, and may be obtained by performing training according to EOG signals of multiple types of blinks of multiple users. Particularly, in this embodiment of the present application, considering individual factors of each user, the method further comprises the following step to further improve the accuracy of recognition:

learning multiple EOG signals of multiple types of blinks of the user, to obtain the at least one reference eigenvalue, the multiple types of blinks comprising the protective blink. According to requirements, the protective blink may further comprise a protective monocular blink and a protective binocular blink.

Further, in an example embodiment, the learning multiple EOG signals comprises:

acquiring at least one training eigenvalue of each EOG signal among the multiple EOG signals; and performing classification analysis on the at least one training eigenvalue of each EOG signal, to obtain the at least one reference eigenvalue.

For example, in an example embodiment, the EOG detection apparatus will instruct the user to perform directive monocular and binocular blinks and protective monocular and binocular blinks for several times and maintain an unconscious blink for a period of time, and records EOG signals; for each blink manner, the EOG detection apparatus extracts an eigenvalue of a characteristic point in the waveform. For example, the eigenvalues in FIG. 2 are used as the training eigenvalues, and classification analysis is then carried out based on these training eigenvalues, to obtain classification models at least comprising the at least one reference eigenvalue; finally, the classification models based on different blink manners are associated with the user (for example, associated with an ID of the user) and stored.

In a possible application scenario of this embodiment of the present application, the device collects an instruction corresponding to the directive blink of the user and use the instruction as a valid control instruction, for example, triggering a camera by means of a blink as described above. However, when blinks of the user are classified into different types, generally, only the unconscious blink of the user is distinguished from other types of blinks, and the other types of blinks generally comprise the directive blink and protective blink described above; except the unconscious blink, the other types of blinks are generally regarded as the directive blinks, which may trigger operation of the device spuriously, and affect user experience. Therefore, by using the method according to this embodiment of the present application, during training of the at least one reference eigenvalue, the multiple types of blinks further comprise the unconscious blink and the directive blink. The directive blink may further comprise a directive monocular blink and a directive binocular blink; in addition, according to the requirement for diversity of control commands, the monocular blink or binocular blink may further comprise two or more continuous monocular blinks or two or more continuous binocular blinks.

In this application scenario, the method according to this embodiment of the present application may further comprise:

determining the blink is an invalid control instruction in response to the blink is the protective blink.

Certainly, the unconscious blink detected also can be determined as an invalid control instruction.

In the foregoing application scenario, the technical solution of this embodiment of the present application can reduce the possibility of misoperation and improve user experience.

Certainly, in other application scenarios, after it is determined that the blink is the protective blink in step S120, the method may further comprise other steps. For example, in a possible application scenario, the EOG detection apparatus is smart glasses, and to prevent eyes of the user from being affected by strong light, when the protective blink is detected, the color of lenses of the smart glasses may be automatically adjusted to be the color of sunglasses.

A person skilled in the art may understand that, in the foregoing method according to the example embodiment of the present application, the serial numbers of the steps do not indicate the sequence for executing the steps, and the sequence for executing the steps should be determined according to functions and internal logic, but should not limit an implementation process of the example embodiment of the present application.

Figure 3:
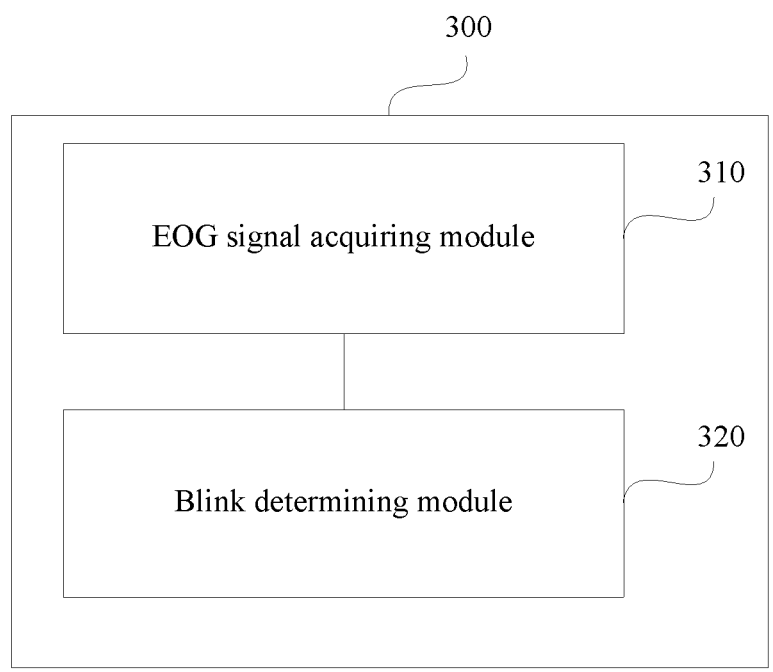
FIG. 3 is a schematic structural diagram of an EOG detection apparatus according to an example embodiment of the present application.

As shown in FIG. 3, an example embodiment of the present application provides an EOG detection apparatus 300, comprising:

an EOG signal acquiring module 310, configured to acquire at least one EOG signal of a blink of at least one eye of a user; and a blink determining module 320, configured to analyze the at least one EOG signal to determine whether the blink is a protective blink.

In this embodiment of the present application, by analyzing the at least one EOG signal, it may be determined whether the blink is a protective blink, thereby distinguishing the protective blink from multiple types of blinks of the user, and providing a basis for further applications related to the protective blink.

The modules of the apparatus in this embodiment of the present application are further described by using the following example embodiments.

Figure 4A:
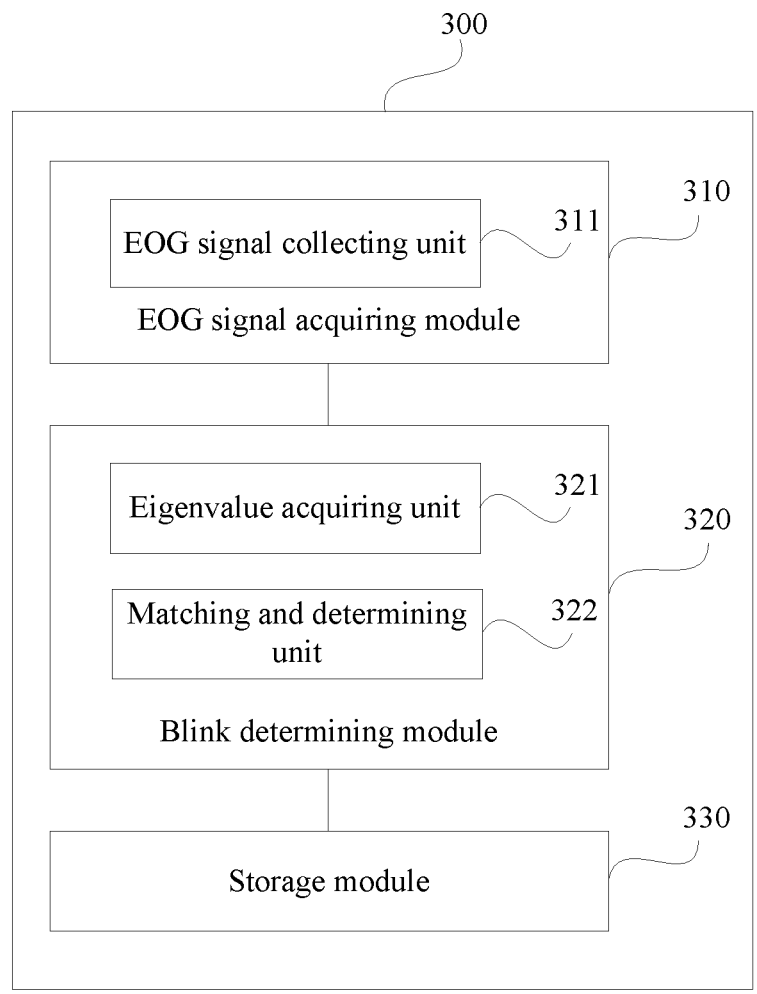
FIG. 4a to FIG. 4c are schematic structural diagrams of three types of EOG detection apparatuses according to example embodiments of the present application.

As shown in FIG. 4a, in an example embodiment, the EOG signal acquiring module 310 comprises:

an EOG signal collecting unit 311, configured to collect the at least one EOG signal.

As described above, the EOG signal collecting unit 311 may comprise, for example, the EOG sensing device described in the foregoing method embodiment. Generally, the EOG sensing device comprises multiple electrodes, used to be attached at multiple positions around the eye socket of the user, for example, the multiple electrodes are separately disposed at the outer canthus, at the inner canthus, above the eyelid, below the eyelid, and at the middle of the forehead, to collect EOG signals generated by movements of the eye of the user. In some example embodiments, the electrodes may be embedded and integrated into the frame of glasses, so as to be used by the user easily.

Figure 4B:
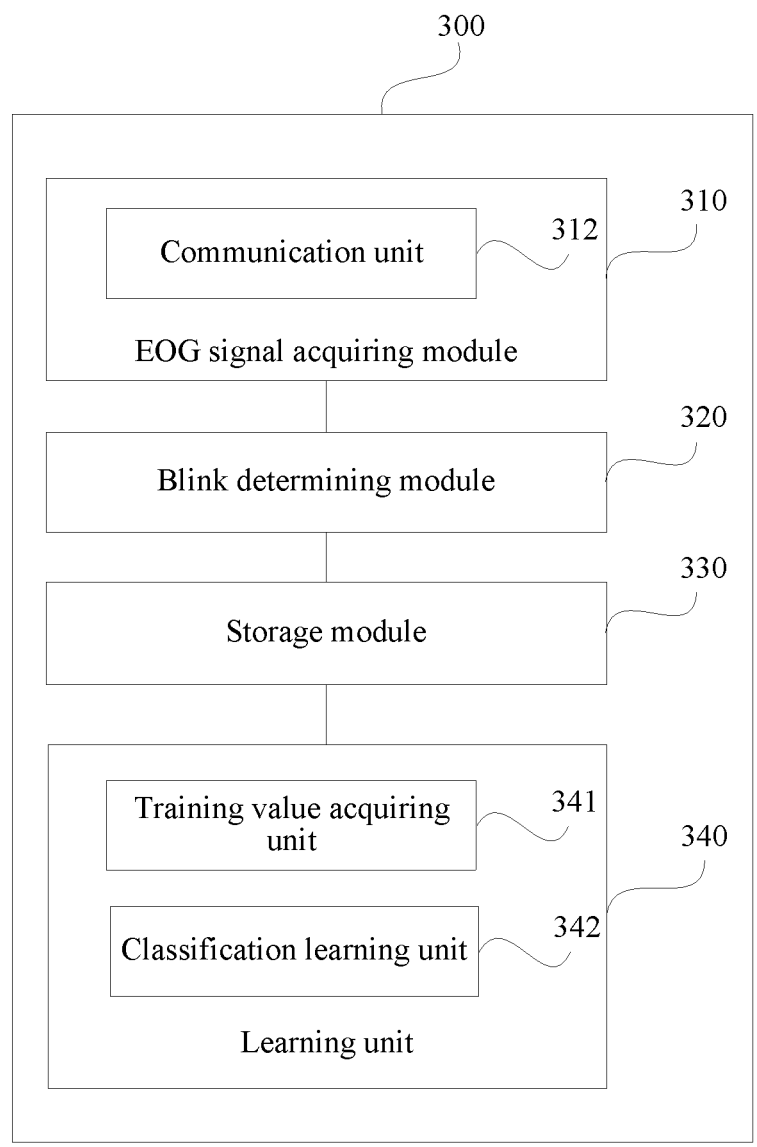

As shown in FIG. 4b, in another example embodiment, the EOG signal acquiring module 310 comprises:

a communication unit 312, configured to receive the at least one EOG signal from an external device.

In this example embodiment, the communication unit 312 may be a wired or wireless communication element, and obtain the at least one EOG signal from an external device or external module by means of communication. For example, the EOG detection apparatus may be set in a user equipment such as a mobile phone or a smart watch, and the user further wears an EOG collecting apparatus, where the EOG detection apparatus may obtain the EOG signal from the EOG collecting apparatus.

In this embodiment of the present application, the blink determining module 320 comprises:

an eigenvalue acquiring unit 321, configured to obtain at least one eigenvalue according to the at least one EOG signal; and a matching and determining unit 322, configured to perform matching on the at least one eigenvalue according to at least one reference eigenvalue, to determine whether the blink is the protective blink.

In this embodiment of the present application, the at least one eigenvalue comprises at least one of the following:

at least one amplitude characteristic of at least one characteristic point of the at least one EOG signal, and at least one time characteristic of at least one characteristic point of the at least one EOG signal.

Certainly, in other example embodiments, the eigenvalue may further comprise other characteristics of the EOG signal, for example, a frequency characteristic.

The at least one eigenvalue may comprise only one eigenvalue, or comprise multiple eigenvalues. When the at least one eigenvalue comprises multiple eigenvalues, the multiple eigenvalues may be multiple amplitude characteristics separately corresponding to multiple characteristic points; or, the multiple eigenvalues may be multiple time characteristics separately corresponding to multiple characteristic points; or at least one eigenvalue of the multiple eigenvalues is at least one amplitude characteristic of at least one characteristic point, and other eigenvalue(s) is(are) time characteristic(s) of at least one characteristic point. Herein, the at least one characteristic point corresponding to the amplitude characteristic may be the same as or different from the at least one characteristic point corresponding to the time characteristic.

For example, in an example embodiment, the characteristic point may be a wave crest of the EOG signal, and the at least one eigenvalue may be an amplitude characteristic corresponding to the wave crest.

For another example, in another example embodiment, the at least one eigenvalue comprises: a time characteristic corresponding to a characteristic point at the beginning of a blink, an amplitude characteristic and a time characteristic of a characteristic point where an amplitude value reaches ½ of a peak value, an amplitude characteristic and a time characteristic corresponding to a wave crest, and the like.

For characteristic points and eigenvalues that may be acquired by the eigenvalue acquiring unit 321, reference may be made to the characteristic points and eigenvalues in the description of FIG. 2 in the foregoing method embodiment.

As shown in FIG. 4*a*, in an example embodiment of the present application, the apparatus 300 further comprises a storage module 330, where the at least one reference eigenvalue is stored in the storage module 330, and the matching and determining unit 322 acquires the at least one reference eigenvalue from the storage module 330.

In another example embodiment of this embodiment of the present application, the at least one reference eigenvalue may be obtained by means of learning training, and may be obtained by performing training according to EOG signals of multiple types of blinks of multiple users. Particularly, in this embodiment of the present application, considering individual factors of each user, as shown in FIG. 4*b*, in an example embodiment, the apparatus 300 further comprises a learning unit 340, configured to learn multiple EOG signals of multiple types of blinks of the user to obtain the at least one reference eigenvalue, so as to further improve the accuracy of recognition, where the multiple types of blinks comprise the protective blink. According to requirements, the protective blink may further comprise a protective monocular blink and a protective binocular blink.

In an example embodiment, the at least one reference eigenvalue may be a value corresponding to the at least one eigenvalue. For example, when the eigenvalue is the amplitude value of the peak, the at least one reference eigenvalue may be one or more reference amplitude values, and during the matching, the amplitude value of the peak may be compared with the one or more reference amplitude values. Certainly, in other example embodiments, the at least one reference eigenvalue may also be a parameter of a classification model for distinguishing different types of blinks comprising the protective blink; the matching may be performed by inputting the at least one eigenvalue to the classification model to obtain a result indicating whether the blink is the protective blink.

Further, in an example embodiment, the learning unit 340 comprises:

a training value acquiring unit 341, configured to acquire at least one training eigenvalue of each EOG signal among the multiple EOG signals; and a classification learning unit 342, configured to perform classification analysis on the at least one training eigenvalue of each EOG signal, to obtain the at least one reference eigenvalue.

In an example embodiment, the training value acquiring unit 341 comprises the EOG sensing device described above; the training value acquiring unit 341 will instruct the user to perform directive monocular and binocular blinks and protective monocular and binocular blinks for several times and maintain an unconscious blink for a period of time, and the EOG sensing device is used to record corresponding EOG signals; for each blink manner, the training value acquiring unit 341 extracts an eigenvalue of a characteristic point in the waveform. For example, the eigenvalues in FIG. 2 are used as the training eigenvalues, and classification analysis is then carried out based on these training eigenvalues, to obtain classification models at least comprising the at least one reference eigenvalue; finally, the classification models based on different blink manners are associated with the user (for example, associated with an ID of the user) and stored in the storage module 330.

In this example embodiment, when the user uses the EOG detection apparatus 300 for the first time, the learning unit 340 is used to perform training learning to obtain at least one reference eigenvalue corresponding to the user, and in subsequent use, the at least one reference eigenvalue may no longer be learned, but directly acquired from the storage module 330.

In an example embodiment, the multiple types of blinks further comprise: an unconscious blink and a directive blink.

Figure 4C:
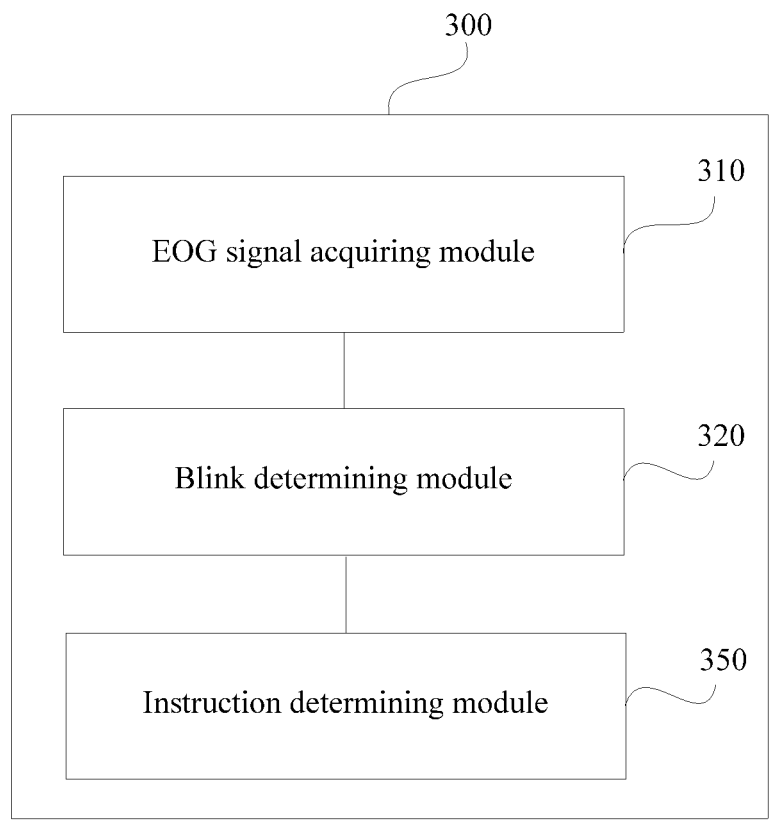

As described above, in a possible application scenario, the device can collect an instruction corresponding to the directive blink of the user and use the instruction as a valid control instruction, for example, triggering a camera by means of a blink as described above. In this case, in addition to determining the protective blink, the EOG detection apparatus 300 further can determine the unconscious blink and directive blink, and exclude the unconscious blink and directive blink from the valid control instruction. Therefore, as shown in FIG. 4*c*, in an example embodiment, the apparatus 300 further comprises:

an instruction determining module 350, configured to determine the blink is an invalid control instruction in response to the blink is the protective blink.

In the foregoing application scenario, the technical solution of this embodiment of the present application can reduce the possibility of misoperation and improve user experience.

Certainly, a person skilled in the art may know that, in other application scenarios, after the blink determining module 320 determines that the blink is the protective blink, the apparatus may further comprise another module corresponding to the determining result. For example, in a possible application scenario, the EOG detection apparatus is smart glasses, and to prevent eyes of the user from being affected by strong light, when the protective blink is determined, the apparatus may further comprise a lens adjusting module, configured to adjust the color of lenses of the smart glasses to be the color of sunglasses automatically, so as to protect the eyes of the user.

Figure 5:
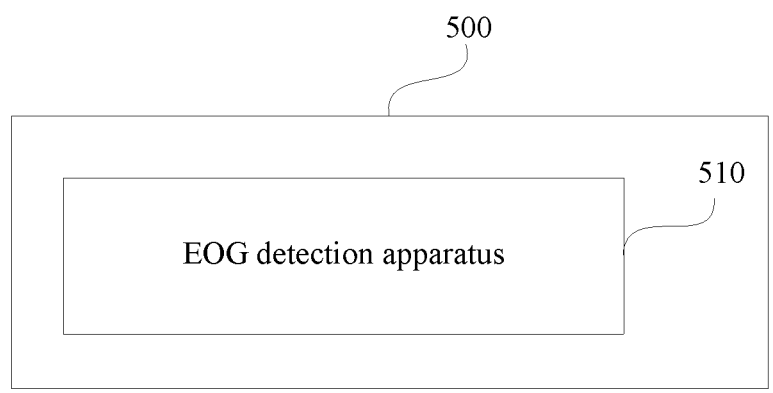
FIG. 5 is a schematic structural diagram of a portable device according to an example embodiment of the present application.

As shown in FIG. 5, a possible embodiment of the present application provides a portable device 500, comprising the EOG detection apparatus 510 described in FIG. 3 or FIG. 4*a* to FIG. 4*c*.

Because the smart glasses are used near eyes of a user, it can conveniently and naturally integrate functions of an EOG sensor. Therefore, in an example embodiment, the portable device is smart glasses.

Certainly, it can be learned from the corresponding description in the foregoing embodiments that, the portable device 500 of this embodiment of the present application may also be other user equipments such as a mobile phone, a tablet computer, a smart watch, and a smart ring.

Figure 6:
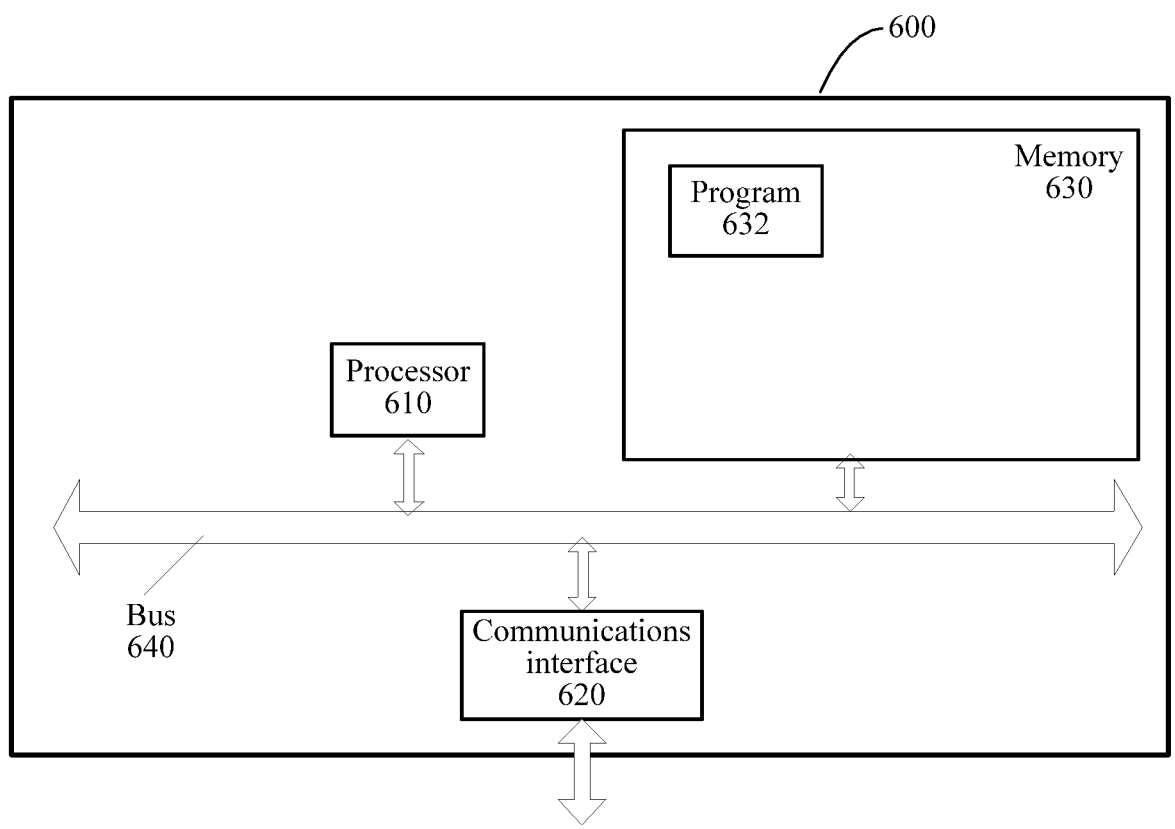
FIG. 6 is a schematic structural diagram of another EOG detection apparatus according to an example embodiment of the present application.

FIG. 6 is a schematic structural diagram of another EOG detection apparatus 600 according to an embodiment of the present application, and this embodiment of the present application does not limit the implementation of the EOG detection apparatus 600. As shown in FIG. 6, the EOG detection apparatus 600 may comprise:

a processor 610, a communications interface 620, a memory 630, and a communication bus 640.

The processor 610, the communications interface 620, and the memory 630 communicate with each other through the communication bus 640.

The communications interface 620 is configured to communicate with a network element such as a client.

The processor 610 is configured to execute a program 632, and may specifically execute related steps in the foregoing method embodiment.

Specifically, the program 632 may comprise program code, and the program code comprises a computer operation instruction.

The processor 610 may be a central processing unit (CPU), or an Application Specific Integrated Circuit (ASIC), or may be configured as one or more integrated circuits for implementing the embodiment of the present application.

The memory 630 is configured to store the program 632. The memory 630 may comprise a high-speed random access memory (RAM), and may also comprise a non-volatile memory, such as at least one disk memory. The program 632 may be specifically configured to cause the EOG detection apparatus 600 to execute the following steps:

acquiring at least one EOG signal of a blink of at least one eye of a user; and analyzing the at least one EOG signal to determine whether the blink is a protective blink.

For implementation of each step in the program 632, reference may be made to the corresponding description of the corresponding step and unit in the foregoing embodiments, and details are not described herein again. It can be clearly understood by a person skilled in the art that, to make the description convenient and concise, for detailed working processes of the foregoing devices and modules, reference may be made to the corresponding process description in the foregoing method embodiment, and details are not described herein again.

A person of ordinary skill in the art may realize that, the units and method steps of examples described with reference to the embodiments disclosed herein may be implemented by electronic hardware, or a combination of computer software and electronic hardware. Whether these functions are executed by hardware or software depends on the particular application and design constraints of the technical solution. A person skilled in the art may use different methods to implement the described functions for each particular application, but such example embodiment should not be regarded as beyond the scope of the present application.

If implemented in the form of software functional units and sold or used as an independent product, the functions may be stored in a computer readable storage medium. Based on such understanding, essence of the technical solution of the present application, or in other words, the part that makes contributions to the prior art, or a part of the technical solution can be embodied in the form of a software product. The computer software product may be stored in a storage medium and comprise several instructions for instructing a computer device (for example, a personal computer, a server, or a network device) to execute all or some steps of the methods according to the embodiments of the present application. The foregoing storage medium comprises: any medium that can store program code, such as a USB flash disk, a removable hard disk, a ROM, a RAM, a magnetic disk, or an optical disc.

The foregoing example embodiments are merely used for describing the present application rather than limiting the present application. A person of ordinary skill in the art may make various modifications and variations without departing from the spirit and scope of the present application, and all the equivalent technical solutions also belong to the scope of the present application. The patent protection scope of the present application shall be subject to the claims.

What is claimed is:

1. A method, applied to a smart glass, comprising:

acquiring, by a system comprising a processor, at least one electrooculogram (EOG) signal of a blink of at least one eye of a user;

analyzing the at least one EOG signal to determine whether the blink is a protective blink;

obtaining at least one eigenvalue according to the at least one EOG signal;

performing matching on the at least one eigenvalue according to at least one reference eigenvalue to determine whether the blink is the protective blink; and adjusting a first color of lenses of the smart glass to be a second color of sunglasses based on determining that the blink is the protective blink.

2. The method of claim 1, wherein the at least one eigenvalue comprises at least one of:

at least one amplitude characteristic of at least one characteristic point of the at least one EOG signal, and at least one time characteristic of the at least one characteristic point of the at least one EOG signal.

3. The method of claim 1, further comprising:
learning multiple EOG signals of multiple types of blinks of the user, to obtain the at least one reference eigenvalue, the multiple types of blinks comprising the protective blink.

4. The method of claim 3, wherein the protective blink comprises at least one of a protective monocular blink or a protective binocular blink.

5. The method of claim 3, wherein the multiple types of blinks further comprise an unconscious blink and a directive blink.

6. The method of claim 3, wherein the learning the multiple EOG signals of the user, to obtain the at least one reference eigenvalue comprises:
acquiring at least one training eigenvalue of each EOG signal among the multiple EOG signals; and
performing classification analysis on the at least one training eigenvalue of each EOG signal, to obtain the at least one reference eigenvalue.

7. The method of claim 1, wherein the acquiring the at least one EOG signal of the blink of the at least one eye of the user comprises:
collecting the at least one EOG signal.

8. The method of claim 1, wherein the acquiring the at least one EOG signal of the blink of the at least one eye of the user comprises:
receiving the at least one EOG signal from an external device.

9. The method of claim 1, further comprising:
determining the blink is an invalid control instruction in response to the blink being determined to be the protective blink.

10. An apparatus, wherein the apparatus is a smart glass, comprising:
a memory that stores executable modules; and
a processor, coupled to the memory, that executes or facilitates execution of the executable modules, comprising:
an electrooculogram (EOG) signal acquiring module configured to receive an EOG signal of a blink of an eye of a user; and
a blink determining module configured to analyze the EOG signal to determine whether the blink is a protective blink,
wherein the blink determining module comprises:
an eigenvalue acquiring unit configured to obtain an eigenvalue according to the EOG signal, and
a matching and determining unit configured to perform matching on the eigenvalue according to a reference eigenvalue, to determine whether the blink is the protective blink, and
wherein a first color of lenses of the smart glass is adjusted to be a second color of sunglasses when it is determined that the blink is the protective blink.

11. The apparatus of claim 10, wherein the executable modules further comprise:
a learning unit configured to learn multiple EOG signals of multiple types of blinks of the user, to obtain the reference eigenvalue, the multiple types of blinks comprising the protective blink.

12. The apparatus of claim 11, wherein the protective blink comprises at least one of a protective monocular blink or a protective binocular blink.

13. The apparatus of claim 11, wherein the multiple types of blinks further comprise an unconscious blink and a directive blink.

14. The apparatus of claim 11, wherein the learning unit comprises:
a training value acquiring unit configured to acquire respective training eigenvalues of each EOG signal among the multiple EOG signals; and
a classification learning unit configured to perform classification analysis on the respective training eigenvalues of each EOG signal, to obtain the reference eigenvalue.

15. The apparatus of claim 14, wherein the executable modules further comprise a storage module configured to store the reference eigenvalue.

16. The apparatus of claim 10, wherein the EOG signal acquiring module comprises:
an EOG signal collecting unit configured to collect the EOG signal.

17. The apparatus of claim 10, wherein the EOG signal acquiring module comprises:
a communication unit configured to receive the EOG signal from an external device.

18. The apparatus of claim 10, wherein the executable modules further comprise:
an instruction determining module configured to determine the blink is an invalid control instruction in response to the blink being determined to be the protective blink.

19. A portable device, comprising the apparatus according to claim 10.

20. A computer readable storage device comprising executable instructions that, in response to execution, cause a device comprising a processor to perform operations, wherein the device is a smart glass, comprising:
acquiring at least one electrooculogram (EOG) signal of at least one blink of at least one eye of at least one user;
analyzing the at least one EOG signal to determine whether the at least one blink is a protective blink;
obtaining at least one eigenvalue according to the at least one EOG signal; and
performing matching on the at least one eigenvalue according to at least one reference eigenvalue to determine whether the blink is the protective blink; and
adjusting a first color of lenses of the smart glass to be a second color of sunglasses based on determining that the blink is a protective blink.

* * * * *